|| United States Patent [19] | [11] Patent Number: 4,760,739 |
| Ichino | [45] Date of Patent: Aug. 2, 1988 |

[54] ULTRASONIC TRANSMIT-RECEIVE PROBE

[75] Inventor: Kouji Ichino, Tokyo, Japan

[73] Assignee: Kaijo Kenki Co., Ltd., Japan

[21] Appl. No.: 877,217

[22] Filed: Jun. 23, 1986

[51] Int. Cl.⁴ ............................................. G01N 29/04
[52] U.S. Cl. ......................................... 73/661; 73/644
[58] Field of Search ...................... 73/661, 644, 866.5,
73/861.28, 861.29, 861.31; 310/336, 327, 341, 344

[56] References Cited

U.S. PATENT DOCUMENTS 3,771,117  11/1973  Shaffer et al. .......................... 310/327
4,096,754   1/1978  Beveridge, Jr. et al. ........... 73/866.5
4,649,754   3/1987  Zacharias ............................. 310/336

Primary Examiner—Stewart J. Levy
Assistant Examiner—Louis M. Arana
Attorney, Agent, or Firm—Steinberg & Raskin

[57] ABSTRACT

An ultrasonic transmit-receive probe is disclosed which is capable of effectively protecting an internal structure of the probe against leaked steam so as to ensure stable and positive operation of the probe over a long period of time. The probe includes an enclosing tube arranged in a probe housing. The enclosing tube is sealedly connected at one end thereof to an oscillator housing receiving an oscillator therein to communicate therewith and sealedly fitted at the other end thereof on a plug received in the other end of the probe housing so as to outwardly project therefrom, thereby sealedly protecting the oscillator and plug against the atmosphere in the probe housing.

18 Claims, 4 Drawing Sheets

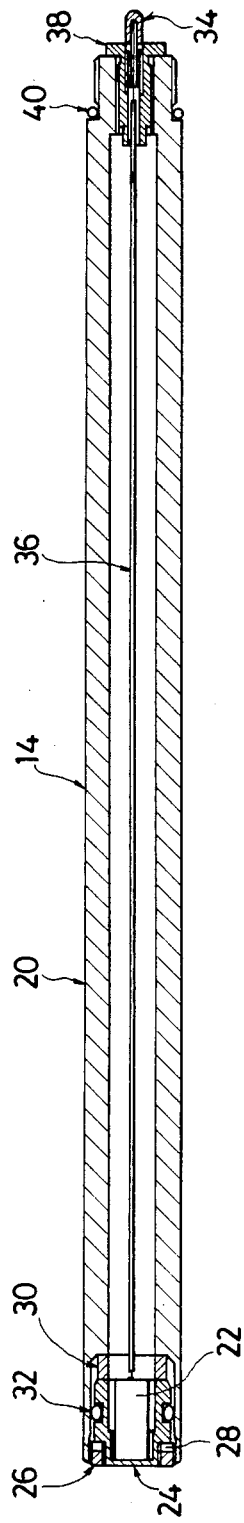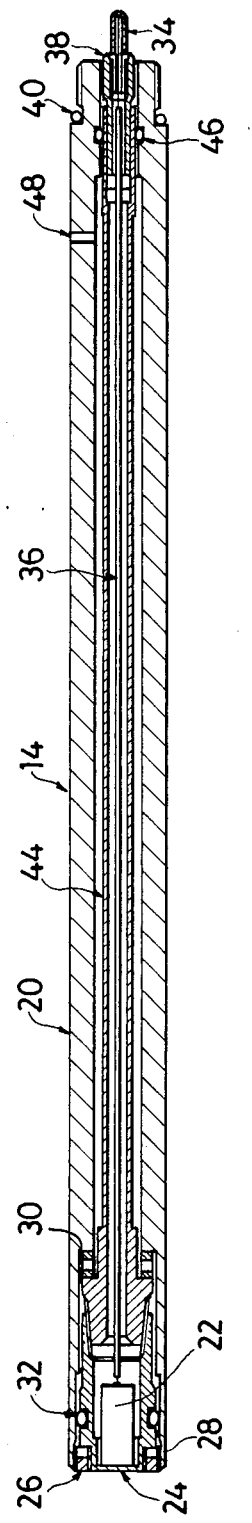

ULTRASONIC TRANSMIT-RECEIVE PROBE

BACKGROUND OF THE INVENTION

1. Field of the Invention

This invention relates to a probe for transmitting and receiving ultrasonic waves (hereinafter referred to as an "ultrasonic transmit-receive probe"), and more particularly to an ultrasonic transmit-receive probe which is adapted to measure the flow velocity and flow rate of moistened fluid of high temperature and high pressure such as steam flowing through a pipe utilizing ultrasonic wave.

2. Description of the Prior Art

A device has been developed and extensively used in a variety of fields which is adapted to propagate ultrasonic waves through gas flowing through a pipe in order to measure the flow velocity and flow rate of the gas by utilizing the variation in propagation velocity of the ultrasonic waves. Such a conventional device for measuring the flow velocity and flow rate of steam utilizing ultrasonic waves is typically constructed in such a manner as shown in FIG. 1. More particularly, the measuring device includes a pair of sockets 10 mounted on a wall of a pipe 12 in a manner to be obliquely opposite to each other at a predetermined angle. In FIG. 1, only one of the sockets 10 is shown for the sake of brevity. Reference numeral 14 designates an ultrasonic transmit-receive probe 14 of which one end is fixedly received in each of the sockets 10 by means of a gas seal unit 16. The conventional measuring device also includes a terminal box 18 connected to the other end of the probe 14, which is then connected to a controller (not shown). The probes 14 insertedly connected to the sockets 10 are adapted to alternately and repeatedly carry out the transmission and reception of an ultrasonic pulse signal controlled by the controller, so that the propagation time of the ultrasonic signal propagated across steam flowing through the pipe 12 may be measured to obtain the flow velocity and flow rate of the steam.

Such an ultrasonic transmit-receive probe 14 employed in the conventional measuring device, as shown in FIG. 2, conventionally comprises a probe housing 20 of a cylindrical shape; an oscillator 22 airtightly or sealedly received in one end of the probe housing 20 by means of an oscillator housing 24, an oscillator holder 26, spacers 28 and 30 and an O-ring 32; and a plug 34 having one end connected through a lead wire 36 insulatedly covered with a tetrafluoroethylene tube to the oscillator 22 and securely held in the probe housing 20 by means of a plug stopper 38 and the other end outwardly projected from the probe housing 14 so as to be inserted into the terminal box 18. Reference numeral 40 indicates an O-ring interposed between the gas seal unit 16 and the probe housing 20.

In the ultrasonic transmit-receive probe 14 constructed as described above, the oscillator 22 is airtightly sealed by means of the O-ring 32. However, if steam is the fluid being measured, the O-ring 32 is exposed to direct contact with the steam. As a result the O-ring maybe constantly subjected to settling, since steam is high in temperature, pressure and activity. Even when the O-ring 32 is formed of the most steam-resistant material, it cannot be full proof against steam having pressure of 10 kg/cm$^2$ at a temperature of about 183° C. Thus, settling of the O-ring 32 occurs in a short period of time, resulting in a failure in sealing.

Such a failure in sealing causes steam to enter the interior of the probe housing 20, resulting in various problems, such as a failure in the insulation of the oscillator 22, a failure in bonding between the oscillator housing 24 and the oscillator 22, hydrolysis of heat-resistant plastic such as polyimide, which forms the spacer 30 and plug stopper 38, and the like; so that a failure in the measuring of the flow velocity and flow rate of steam occurs in a short period of time. Accordingly, it is necessary to frequently replace the probe. Further, when hydrolysis of the plug stopper 38 leads to the leakage of steam, the terminal box 18 insulation fails. Thus, it is also necessary to often replace the terminal box 18.

Thus, the conventional ultrasonic transmit-receive probe soon deteriorates in operational reliability eventhough it is necessary for such a probe to operate stably over a long period of time.

Accordingly, it would be highly desirable to develop an ultrasonic transmit-receive probe which is capable of operating stably and effectively over a long period of time and also capable of being positively protected against leaked steam.

SUMMARY OF THE INVENTION

Generally speaking, in accordance with the present invention, an ultrasonic transmit-receive probe is provided. The ultrasonic transmit-receive probe includes a probe housing, an oscillator housing received in one end of the probe housing, an oscillator received in the oscillator housing and a plug received in the other end of the probe housing so as to outwardly project from the probe housing and electrically connected to the oscillator.

Also, the ultrasonic transmit-receive probe of the present invention includes enclosing means arranged in the probe housing. The enclosing means are sealedly connected between the oscillator housing and the plug to sealedly protect the oscillator and plug against the atmosphere in the probe housing, so that even when the leakage of steam into the interior of the probe housing occurs, the oscillator and plug may be effectively protected against the leaked steam.

In a preferred embodiment of the present invention, the enclosing means comprise an enclosing tube sealedly connected at one end thereof to the oscillator housing so as to communicate therewith and sealedly fitted at the other end thereof on the plug.

Also, the ultrasonic transmit-receive probe of the present invention may include reverberation preventing means. In a preferred embodiment of the present invention, the reverberation preventing means comprise damping means provided on the enclosing tube.

Accordingly, it is an object of the present invention to provide an ultrasonic transmit-receive probe which is capable of operating stably and efficiently over a long period of time.

It is another object of the present invention to provide an ultrasonic transmit-receive probe which, because it is capable of eliminating deterioration of operational reliability due to the settling of an O-ring or the like, does not have to be replaced.

It is a further object of the present invention to provide an ultrasonic transmit-receive probe which is capable of positively protecting an internal structure of the probe against leaked steam.

It is still another object of the present invention to provide an ultrasonic transmit-receive probe which is capable of effectively preventing an input signal from being disturbed due to a reverberation phenomenon.

It is still a further object of the present invention to provide an ultrasonic transmit-receive probe which is capable of accomplishing the above-noted objects with a simple structure.

Still other objects and advantages of the invention will in part be obvious and will in part be apparent from the specification.

The invention accordingly comprises the features of construction, combination of elements, and arrangement of parts which will be exemplified in the construction hereinafter set forth.

BRIEF DESCRIPTION OF THE DRAWINGS

For a fuller understanding of the invention, reference is made to the following description taken in connection with the accompanying drawings in which like reference numerals designate like or corresponding parts throughout, in which:

FIG. 2 is a side elevation view in section detailedly showing the conventional probe of FIG. 1;

FIG. 3 is a side elevation view in section showing an embodiment of an ultrasonic transmit-receive probe according to the present invention;

DETAILED DESCRIPTION OF THE PREFERRED EMBODIMENT

Figure 1:
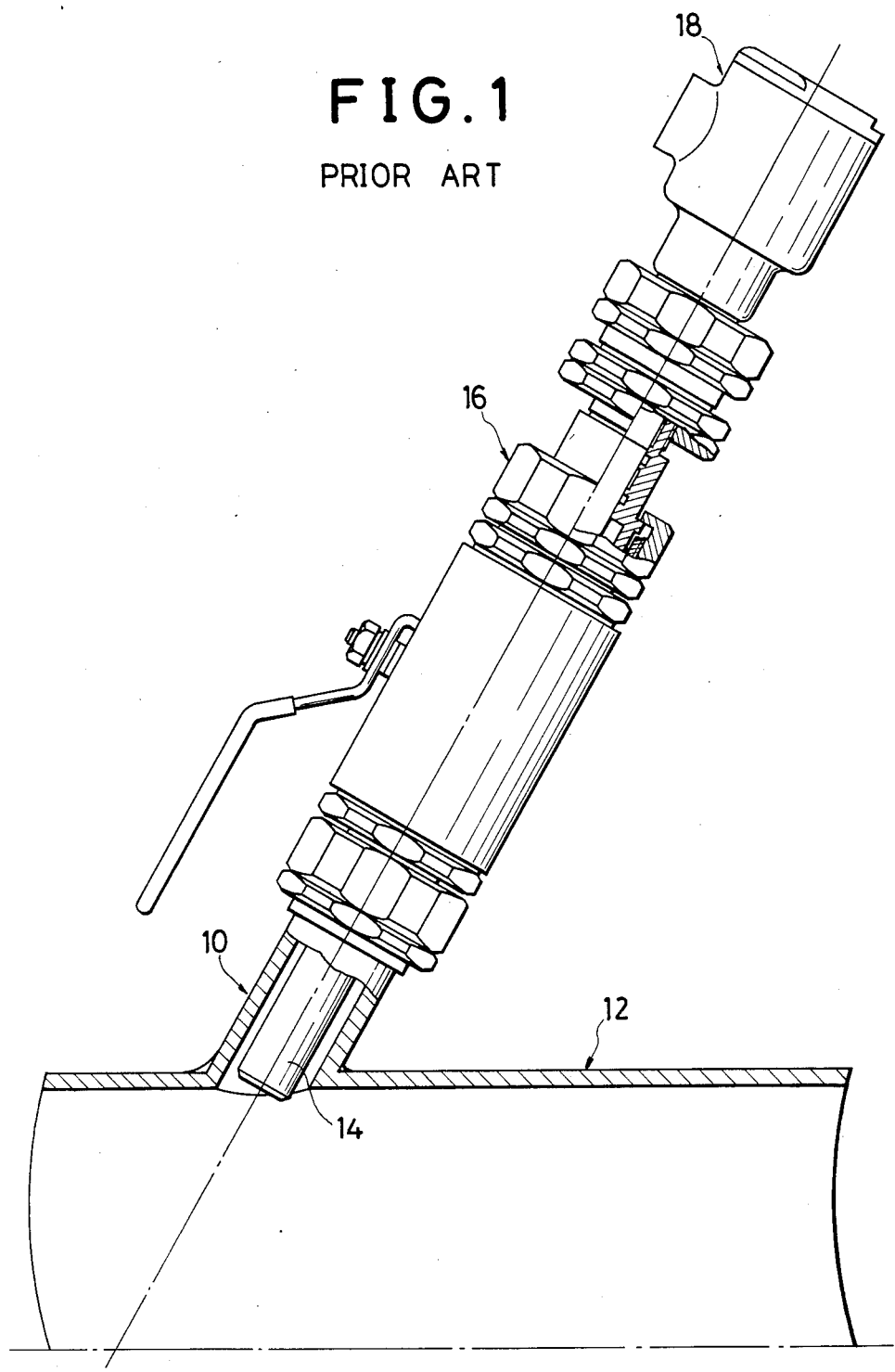
FIG. 1 is a front elevation view partly in section showing the manner of mounting of a conventional ultrasonic transmitreceive probe with respect to a pipe.
Figure 4:
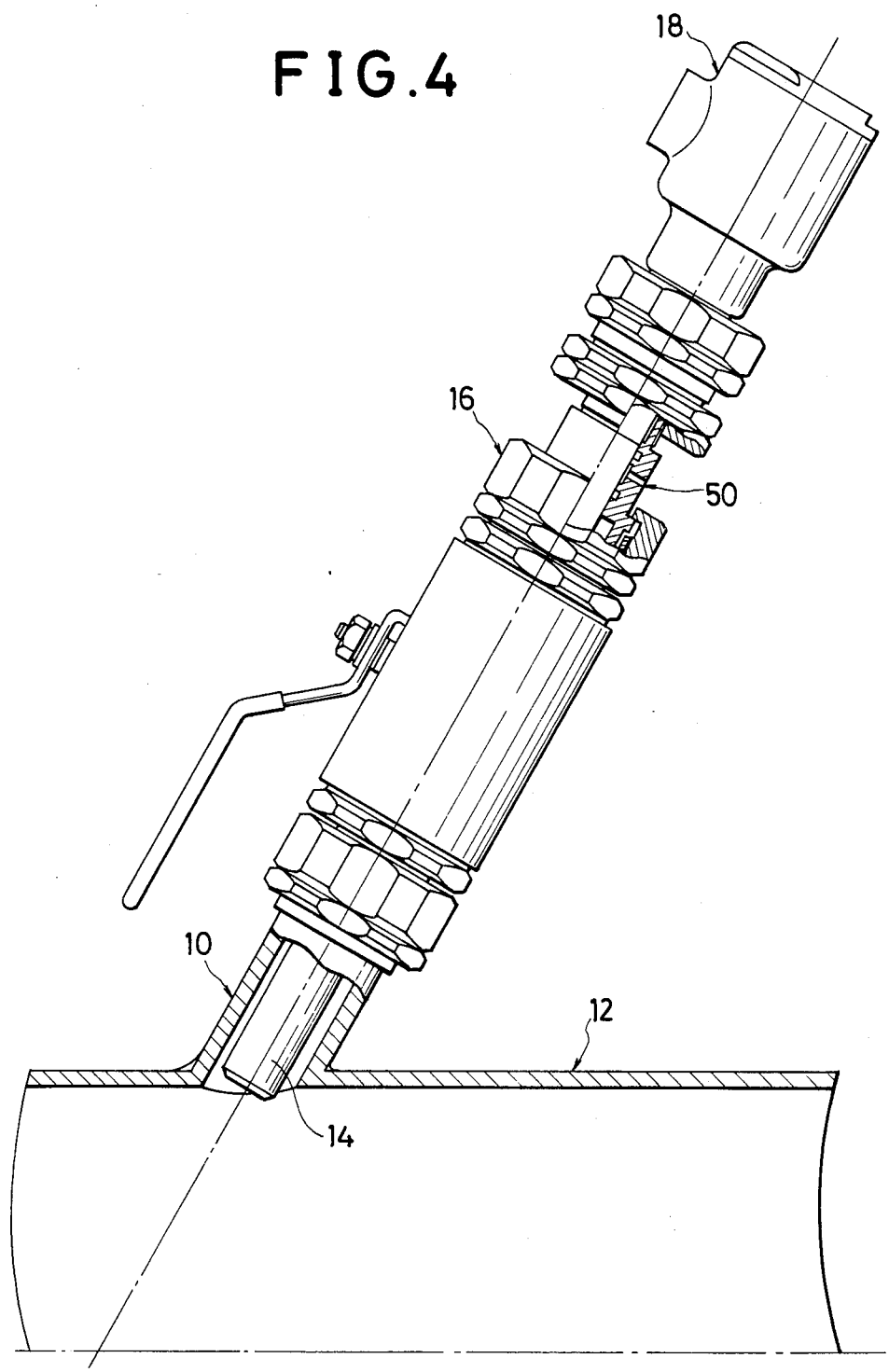
FIG. 4 is a front elevation view partly in section showing the manner of mounting of the ultrasonic transmit-receive probe shown in FIG. 3 with respect to a pipe.
Figure 5:
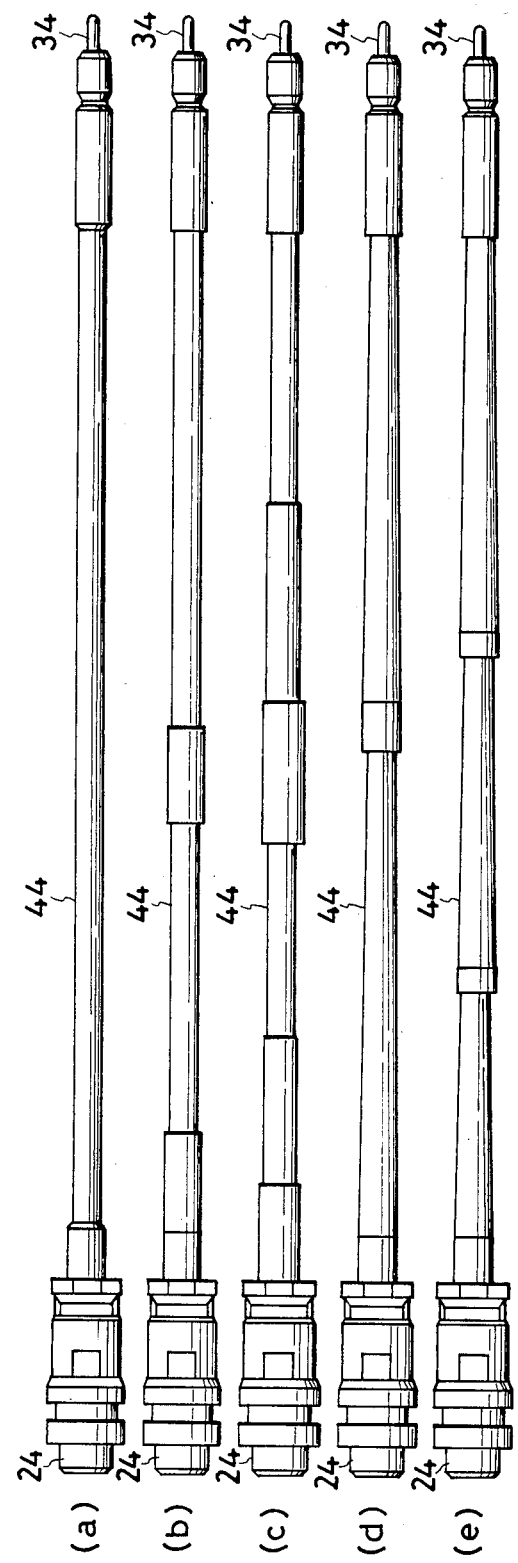
FIGS. 5(a) to 5(e) each are a side elevation view showing an outer shape of an ultrasonic transmit-receive probe according to the present invention, particularly an enclosing tube.

Now, an ultrasonic transmit-receive probe according to the present invention will be described hereinafter with reference to FIGS. 3 to 5.

FIG. 3 illustrates an embodiment of an ultrasonic transmit-receive probe according to the present invention. An ultrasonic transmit-receive probe of the illustrated embodiment which is generally designated by reference numeral 14 includes a probe housing 20, an oscillator 22 received in one end of the probe housing 20 through an oscillator housing 24 and a plug 34 received in the other end of the probe housing 20 in a manner to outwardly project therefrom. The ocillator housing 24 is formed of a suitable metal material such as titanium. The oscillator 22 is electrically connected through a lead wire 36 insulatedly covered with a tetrafluoroethylene tube to the plug 34.

The probe of the embodiment shown in FIG. 3 also includes enclosing means for sealedly protecting an internal structure of the probe such as the oscillator 22, the oscillator housing 24 and the like against leaked steam. In the illustrated embodiment, the enclosing means comprise an enclosing tube 44 formed of a metal material and arranged to extend between the oscillator housing 24 and the plug 34 in the probe housing 20. The enclosing tube 44 is airtightly or sealedly connected at one end to the oscillator housing 24 so as to communicate therewith and airtightly or sealedly fitted at the other end thereof to the plug 34 and substantially receives the lead wire 36 therein. More particularly, the enclosing tube 44 is threadedly fitted at one end thereof in the oscillator housing 24 to sealedly receive the oscillator 22 and at the other end thereof on a plug stopper 38 receiving the plug 34 therein, to thereby sealedly receive the oscillator 22 in a space defined by a combination of the oscillator housing 24 and the enclosing tube 44 and isolate the plug from the atmosphere in the probe housing.

The enclosing tube 44 is securely held in the probe housing 20 in such a manner as to airtightly or sealedly hold the oscillator housing 24 in one end of the probe housing 20 by means of a housing holder 26, a spacer 28 and an O-ring 32; concurrently a spacer 30 is interposed between the probe housing 20 and the enclosing tube 44; and then the plug stopper 38 is held in the other end of the probe housing 20 by means of an O-ring 46 interposed therebetween.

The probe housing 20 is formed with at least a throughhole 48 of a small diameter through which the interior of the probe housing 20 communicates to the exterior thereof so as to constantly keep the pressure in the probe housing 20 at atmospheric pressure.

In the illustrated embodiment, the spacers 28 and 30 and the plug stopper 38 are preferably formed of a plastic material having a steam-resistant property as well as a heat-resistant property such as, for example, polyether ether ketone (PEEK) or the like.

The connection of the enclosing tube 44 to the oscillator housing 24 and plug stopper 38 may be carried out by welding. However, it is preferably carried out by such threaded engagement as described above or by flange connection, because such a connection manner highly facilitates the assembling and disassembling of the probe 14.

The remaining part of the probe 14 may be constructed in substantially the same manner as the conventional probe shown in FIG. 2.

Now, the manner of mounting of the ultrasonic transmitreceive probe of the illustrated embodiment described above with respect to a pipe through which steam is flowed will be described with reference to FIG. 4.

First, one end of the probe 14 is connected to a terminal box 18 and the other end thereof is received in a socket 10 of a pipe 12. Then, the probe 14 is fixed to the socket 10 by means of a gas seal unit 16 according to the conventional procedure. The gas seal unit 16 is preferably formed with a communication hole 50 through which the interior of the gas seal unit 16 is communicated to the exterior thereof. Such construction, when steam leaks into the probe 14 due to a failure in sealing, allows the steam to be discharged through the throughhole 48 (FIG. 3) of the probe housing 20 (FIG. 3) and communication hole 50 to ambient atmosphere while the enclosing tube 44 (FIG. 3) effectively protects the oscillator 22 (FIG. 3) against the steam, thereby ensuring that the probe 14 constantly and positively accomplishes the function of transmitting and receiving ultrasonic waves.

In the illustrated embodiment, as described above, the oscillator 22 is sealedly received in the oscillator housing 24 by means of the enclosing tube 44 so as to be protected against leaked steam. However, such construction occasionally causes damped oscillation to remain in the enclosing tube after the probe 14 transmits an ultrasonic wave. Such damped oscillation causes a reverberation phenomenon which disturbs the input signal when the probe receives an ultrasonic wave. Such a disadvantage may be overcome by forming the enclosing tube 44 of a damping material such as vibration proof metal, plastic or the like. This disadvantage may also be effectively prevented by covering a suitable portion of the enclosing tube 44 with a suitable damping material or covering the whole enclosing tube 44 with a damping material such as heat-shrinkable tetrafluoroethylene. Alternatively, this disadvantage may be overcome by varying the thickness of the enclosing tube 44 at least partially or by stages to vary acoustic impedance, as shown in FIGS. 5(a) to 5(e).

As can be seen from the foregoing, the ultrasonic transmit-receive probe of the present invention, even if leakage of steam occurs, effectively sealedly protects the oscillator and the plug against leaked steam and discharges the steam to ambient atmosphere, thereby ensuring the stable and positive operation of the probe over a long period of time with complete reliability. Also, the present invention is capable of effectively preventing a reverberation phenomenon.

It will thus be seen that the objects set forth above, among those made apparent from the preceding description, are efficiently attained and, since certain changes may be made in the above construction without departing from the spirit and scope of the invention, it is intended that all matter contained in the above description or shown in the accompanying drawings shall be interpreted as illustrative and not in a limiting sense.

What is claimed is:

1. An ultrasonic transmit-receive probe comprising:
   a probe housing;
   said probe housing being formed with at least one through-hole via which the interior of said probe housing communicates with ambient atmosphere;
   an oscillator housing received in one end of said probe housing;
   an oscillator received in said oscillator housing;
   a plug electrically connected to said oscillator and received in the other end of said probe housing so as to outwardly project therefrom; and
   enclosing means arranged in said probe housing in a manner to be sealedly connected between said oscillator housing and said plug to sealedly isolate at least said oscillator in said oscillator housing from an interior of said probe housing;
   wherein said enclosing means comprise an enclosing tube airtightly or sealingly connected at one end thereof to said oscillator housing so as to communicate therewith and at the other end thereof to said plug, and being spaced from an inner surface of said probe housing in the interior thereof.

2. An ultrasonic transmit-receive probe as defined in claim 1 further comprising reverberation preventing means.

3. The probe of claim 1, additionally comprising a lead wire electrically interconnecting said oscillator and plug, and extending through said tube.

4. The probe of claim 1, additionally comprising a spacer interposed between said probe housing and enclosing tube.

5. The probe of claim 1, additionally comprising a stopper for retaining said plug in said housing.

6. The probe of claim 5, additionally comprising an O-ring situated between said tube and said probe housing, for securely retaining said stopper in said housing.

7. The probe of claim 5, wherein said enclosing tube is connected to said oscillator housing and stopper by welding.

8. An ultrasonic transmit-receive probe as defined in claim 5, wherein said enclosing tube is threadedly connected to said oscillator housing and said plug stopper.

9. An ultrasonic transmit-receive probe as defined in claim 5, wherein said enclosing tube is connected to said oscillator housing and said plug stopper by means of flange connection.

10. An ultrasonic transmit-receive probe as defined in claim 1, wherein reverberation preventing means are provided on said enclosing tube.

11. An ultrasonic transmit-receive probe as defined in claim 10, wherein said reverberation preventing means comprise said enclosing tube formed of damping material.

12. An ultrasonic transmit-receive probe as defined in claim 10, wherein said reverberation means comprise said enclosing tube being formed of thickness at least partially varied.

13. An ultrasonic transmit-receive probe as defined in claim 10, wherein said reverberation means comprise said enclosing tube having a thickness varied by stages.

14. An ultrasonic transmit-receive probe as defined in claim 10, wherein said reverberation preventing means comprise damping means provided on said enclosing tube.

15. An ultrasonic transmit-receive probe as defined in claim 14, wherein said damping means comprise a cover member formed of a damping material and arranged to cover at least a part of said enclosing tube.

16. An ultrasonic transmit-receive probe as defined in claim 15, wherein said cover member is formed of heat-shrinkable tetrafluoroethylene.

17. An ultrasonic transmitreceive probe comprising:
    a probe housing;
    said probe housng being formed with at least one through-hole via which an interior of said probe housing communicates with an exterior thereof;
    an oscillator housing received in one end of said probe housing;
    an oscillator received in said oscillator housing;
    a plug electrically connected to said oscillator and received in the other end of said probe housing so as to outwardly project therefrom; and
    an enclosing tube arranged in said probe housing in a manner to be airtightly or sealingly connected at one end thereof to said oscillator housing to communicate therewith and airtightly or sealingly fitted at the other end thereof on said plug to sealedly protect said oscillator and plug against atmosphere in said probe housing between said tube and said probe housing.

18. An ultrasonic transmitreceive probe comprising:
    a probe housing;
    said probe housing being formed with at least one through-hole via which an interior of said probe housing communicates with an exterior thereof;
    an oscillator housing received in one end of said probe housing;
    an oscillator received in said oscillator housing;
    a plug electrically connected to said oscillator and received in the other end of said probe housing so as to outwardly project therefrom;
    an enclosing tube arranged in said probe housing in a manner to be airtightly or sealingly connected at one end thereof to said oscillator housing to communicate therewith and airtightly or sealingly fitted at the other end thereof on said plug to sealedly protect said oscillator and plug against atmosphere in said probe housing; and
    reverberation preventing means provided on said enclosing tube.

* * * * *

UNITED STATES PATENT AND TRADEMARK OFFICE
CERTIFICATE OF CORRECTION

PATENT NO. : 4,760,739
DATED : August 2, 1988
INVENTOR(S) : Kouji Ichino

It is certified that error appears in the above-identified patent and that said Letters Patent is hereby corrected as shown below:

On the title page assignee should read

--(73) Assignee: Kaijo Denki Co. Ltd., Japan --.

Signed and Sealed this

Twenty-eighth Day of February, 1989

Attest:

DONALD J. QUIGG

Attesting Officer

Commissioner of Patents and Trademarks